(12) United States Patent
Heinelt et al.

(10) Patent No.: US 8,067,614 B2
(45) Date of Patent: Nov. 29, 2011

(54) N-SUBSTITUTED (BENZOIMIDAZOL-2-YL)PHENYLAMINES, PROCESSES FOR THEIR PREPARATION, THEIR USE AS A MEDICAMENT OR DIAGNOSTIC AID, AND A MEDICAMENT COMPRISING THEM

(75) Inventors: Uwe Heinelt, Weisbaden (DE); Hans-Jochen Lang, Hofheim (DE); Armin Hofmeister, Oppenheim (DE); Klaus Wirth, Kriftel (DE); Martin Hug, Freiburg (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 12/722,634

(22) Filed: Mar. 12, 2010

(65) Prior Publication Data
US 2010/0168196 A1 Jul. 1, 2010

Related U.S. Application Data

(63) Continuation of application No. 12/027,033, filed on Feb. 6, 2008, now abandoned, which is a continuation of application No. 10/770,654, filed on Feb. 3, 2004, now abandoned.

(60) Provisional application No. 60/477,569, filed on Jun. 11, 2003.

(30) Foreign Application Priority Data

Feb. 4, 2003 (DE) .................................. 103 04 294

(51) Int. Cl.
*A61K 31/4184* (2006.01)
*C07D 235/30* (2006.01)

(52) U.S. Cl. .................................... 548/307.4; 514/395

(58) Field of Classification Search ................ 548/307.4
See application file for complete search history.

(56) References Cited

U.S. PATENT DOCUMENTS

| | | | |
|---|---|---|---|
| 6,005,010 A | 12/1999 | Schwark et al. | |
| 6,518,291 B1 | 2/2003 | Saunders et al. | |
| 6,686,384 B2 | 2/2004 | Hofmeister et al. | |
| 6,825,231 B2 | 11/2004 | Heinelt et al. | |
| 6,958,357 B2 | 10/2005 | Hofmeister et al. | |
| 7,049,333 B2 | 5/2006 | Lang et al. | |
| 7,442,717 B2 | 10/2008 | Heinelt et al. | |

FOREIGN PATENT DOCUMENTS

| | | |
|---|---|---|
| GB | 1131191 | 10/1968 |
| JP | 02306916 | 12/1990 |
| JP | 10330369 | 12/1998 |
| WO | WO 90/14338 | 11/1990 |
| WO | WO 01/21160 | 3/2001 |
| WO | WO 01/21582 | 3/2001 |
| WO | WO 01/72742 | 10/2001 |
| WO | WO 01/79186 | 10/2001 |
| WO | WO 02/20496 | 3/2002 |
| WO | WO 02/46169 | 6/2002 |

OTHER PUBLICATIONS

U.S. Appl. No. 09/975,566, filed Oct. 11, 2001, Collins, et al.
Akhter, et al., Squalamine, a Novel Cationic Steroid, Specifically Inhibits the Brush-border Na+/H+ Exchanger isoform NHE3, The American Physiological Society, 1999, c136-c144.
Ernsberger, et al., Clonidine Binds To Imidazole Binding Sites As Well As Alpha2-Adrsnoceptors in The Ventolateral Medulla, European Journal of Pharmacology, 134 (1987) 1-13.
Fliegel, et al., Regulation And Characterization Of The Na+/H+ Exchanger, Biochem. Cell. Biol., 76: (1998), 735-741.
Jacobson, et al., Chem. Ber. (1908), 41, 524.
Janssens, et al., New Antihistaminic N-Heterocyclic 4-Piperidinamines. 1 Synthesis and Antihistaminic Activity of N-(4-Piperidinyl)-1H-Benzimidazol-2-Amines. J. Med. Chem. (1985), 28, 1925-1933.
Jen, et al., Amidines and Related Compounds. 6. Studies on Structure-Activity Relationships of Antihypertensive and Antisecretory Agents Related to Cloridine, Journal of Medicinal Chemistry, 1975, vol. 18, No. 1., 90-99.
Ma, et al., Expression And Localization Of Na+/H+ Exchangers In Rat Central Nervous System, Neuroscience, (1997), vol. 79, No. 2, pp. 591-603.
Mohsen, et al., The Cyclodesulfurization Of Thio Compounds; VII. A New Facile Synthesis Of Na-Substituted Benzimidazoles, Synthesis Communication, Jan. 1974, S. 41-42.
Nishi, T., et al., Blood Platelet Adhesion Inhibitor, An english Translation of JP 02/306,916 (1990).
Oriowski, et al., Molecular Cloning Of Putative Members Of The Na/H Exchanger, J. Biological Chemistry, 1992, vol. 267, 9331-9339.
Rastogi, et al., 2-Aminobenzimidazoles in Organic Syntheses , Synthesis. (1983), 861-882.
Tuncbilek, et al., Synthesis And Antimicrobial Activity Of Some New Anilino Benzimidazoles, Arch. Pharm. Pharm. Med. Chem., (1997), 330 (12), 372-376.
Wu, et al., 1-Cyanoimidazole As A Mild And Efficient Electrophilic Cyanating Agent, Organic Letters, 2000, vol. 2, No. 6, 795-797.

*Primary Examiner* — Laura L. Stockton
(74) *Attorney, Agent, or Firm* — Jiang Lin; Scully, Scott, Murphy & Presser, P.C.

(57) ABSTRACT

This invention is directed to the compound of formula (I), compositions containing said compounds to inhibit the sodium-proton exchanger of subtype 3 (NHE3) which are useful in the prevention or treatment of various disorders in a patient suffering from a disease state, such as, renal disorders including acute or chronic renal failure, disorders of biliary function and for respiratory disorders such as snoring or sleep apnea or for stroke.

4 Claims, No Drawings

N-SUBSTITUTED (BENZOIMIDAZOL-2-YL)PHENYLAMINES, PROCESSES FOR THEIR PREPARATION, THEIR USE AS A MEDICAMENT OR DIAGNOSTIC AID, AND A MEDICAMENT COMPRISING THEM

This application is a Continuation of application Ser. No. 12/027,033, filed Feb. 6, 2008, which is a Continuation of application Ser. No. 10/770,654, filed Feb. 3, 2004, now abandoned, which claims the benefit of U.S. Provisional Application No. 60/477,569, filed Jun. 11, 2003, all of which are incorporated herein by reference in their entireties.

FIELD OF THE INVENTION

The invention relates to compounds of the type of N-substituted (benzoimidazol-2-yl)phenylamines which inhibit the sodium-proton exchanger of subtype 3 (NHE3) and which are useful in the prevention or treatment of various disorders. Thus, the compounds can be employed, inter alia, for renal disorders such as acute or chronic renal failure, for disorders of biliary function, for respiratory disorders such as snoring, sleep apneas or for stroke.

SUMMARY OF THE INVENTION

The invention relates to compounds of the formula I

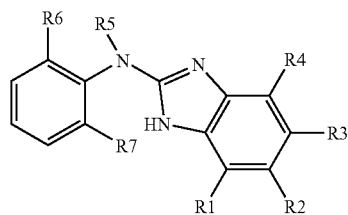

in which the meanings are:
R1 and R4
  independently of one another H, F, Cl, Br, alkyl having 1, 2, 3 or 4 carbon atoms or alkoxy having 1, 2, 3 or 4 carbon atoms,
    where the alkyl and alkoxy groups are unsubstituted or are substituted independently of one another by 1, 2, 3, 4, 5, 6, 7, 8 or 9 F atoms;
R2 and R3
  independently of one another H, F, alkyl having 1, 2, or 3 carbon atoms, alkoxy having 1, 2 or 3 carbon atoms or OH,
    where the alkyl and alkoxy groups are unsubstituted or are substituted independently of one another by 1, 2, 3, 4, 5, 6 or 7 F atoms;
R5
  alkyl having 1, 2, 3 or 4 carbon atoms, alkenyl having 2, 3 or 4 carbon atoms or cycloalkyl having 3, 4 or 5 carbon atoms,
    where the alkyl, alkenyl and cycloalkyl groups are unsubstituted or are substituted by 1, 2, 3, 4, 5, 6, 7, 8 or 9 F atoms;
R6 and R7
  independently of one another H, F, Cl, Br, alkyl having 1, 2 or 3 carbon atoms or alkoxy having 1, 2 or 3 carbon atoms,
    where the alkyl and alkoxy groups are unsubstituted or are substituted independently of one another by 1, 2, 3, 4, 5, 6, 7, 8 or 9 F atoms,
  and at least one of the two radicals R6 or R7 does not correspond to hydrogen;
and the pharmaceutically acceptable salts and trifluoroacetic acid salts thereof.
Preference is given to compounds of the formula I in which the meanings are:
R1 and R4
  independently of one another H, F, Cl, Br, alkyl having 1, 2, 3 or 4 carbon atoms or alkoxy having 1, 2, 3 or 4 carbon atoms,
    where the alkyl and alkoxy groups are unsubstituted or are substituted independently of one another by 1, 2, 3, 4, 5, 6, 7, 8 or 9 F atoms;
R2 and R3
  independently of one another H, F, alkyl having 1, 2 or 3 carbon atoms, alkoxy having 1, 2 or 3 carbon atoms or OH,
    where the alkyl and alkoxy groups are unsubstituted or are substituted independently of one another by 1, 2, 3, 4, 5, 6 or 7 F atoms;
R5
  alkyl having 1, 2, 3 or 4 carbon atoms, alkenyl having 2, 3 or 4 carbon atoms or cycloalkyl having 3, 4 or 5 carbon atoms,
    where the alkyl, alkenyl and cycloalkyl groups are unsubstituted or are substituted by 1, 2, 3, 4, 5, 6, 7, 8 or 9 F atoms;
R6 and R7
  independently of one another F, Cl, Br, alkyl having 1, 2 or 3 carbon atoms or alkoxy having 1, 2 or 3 carbon atoms,
    where the alkyl and alkoxy groups are unsubstituted or are substituted independently of one another by 1, 2, 3, 4, 5, 6 or 7 F atoms;
  and at least one of the two radicals R6 or R7 does not correspond to hydrogen;
and the pharmaceutically acceptable salts and trifluoroacetic acid salts thereof.

Compounds of the formula I preferred in one embodiment are those in which R1 and R4 are described independently of one another by H or F.

Compounds of the formula I preferred in a further embodiment are those in which R2 and R3 are described independently of one another by H or F.

Compounds of the formula I preferred in a further embodiment are those in which R5 is described by methyl, ethyl, isopropyl, allyl or cyclopentyl.

Compounds of the formula I preferred in a further embodiment are those in which R6 and R7 are described independently of one another by F, Cl, Br or methyl, and compounds in which R6 and R7 are described by Cl are particularly preferred.

Compounds of the formula I preferred in a further embodiment are those in which R6 and R7 are not described by hydrogen.

The following compounds of the formula I are very particularly preferred:
(1H-benzoimidazol-2-yl)(2,6-dichlorophenyl)methylamine,
(1H-benzoimidazol-2-yl)(2,6-dichlorophenyl)ethylamine,
(2,6-dichlorophenyl)(5-fluoro-1H-benzoimidazol-2-yl) methylamine,
(1H-benzoimidazol-2-yl)(2,6-dichlorophenyl)isopropylamine allyl(1H-benzoimidazol-2-yl)(2,6-dichlorophenyl)amine, or (1H-benzoimidazol-2-yl)cyclopentyl(2,6-dichlorophenyl)amine and the pharmaceutically acceptable salts and trifluoroacetic acid salts thereof.

If the substituents R1, R2, R3, R4, R5, R6 or R7 contain one or more centers of asymmetry, they may independently of one another have both the S and the R configuration. The compounds may be in the form of optical isomers, of diastereomers, of racemates or of mixtures thereof in all ratios.

The present invention includes all tautomeric forms of the compounds of the formula I.

DETAILED DESCRIPTION OF THE INVENTION

Definition of Terms

As used above, and throughout the description of the invention, the following terms, unless otherwise indicated, shall be understood to have the following meanings "Patient" includes both human and other mammals.

"Pharmaceutically effective amount" is meant to describe an amount of a compound, composition, medicament or other active ingredient effective in producing the desired therapeutic effect.

"Optionally substituted" means either unsubstituted or substituted one or more times by substituents, which may be the same, or different.

Alkyl radicals may be straight-chain or branched. This also applies when they have substituents or occur as substituents of other radicals, for example in fluoroalkyl radicals or alkoxy radicals. Examples of alkyl radicals are methyl, ethyl, n-propyl, isopropyl(=1-methylethyl), n-butyl, isobutyl(=2-methylpropyl), sec-butyl(=1-methylpropyl), tert-butyl(=1,1-dimethylethyl). Preferred alkyl radicals are methyl, ethyl, isopropyl. One or more, for example 1, 2, 3, 4, 5, 6, 7, 8 or 9, hydrogen atoms in alkyl radicals may be replaced by fluorine atoms. Examples of such fluoroalkyl radicals are trifluoromethyl, 2,2,2-trifluoroethyl, pentafluoroethyl, heptafluoroisopropyl. Substituted alkyl radicals may be substituted in any positions.

Alkenyl radicals may be straight-chain or branched. This also applies when they have substituents, for example in fluoroalkenyl radicals. The alkenyl radicals may be unsaturated in various positions and also polyunsaturated. Examples of alkenyl radicals are ethenyl, n-prop-1-enyl, n-prop-2-enyl, isoprop-1-enyl(=1-methylethenyl), n-but-1-enyl, n-but-2-enyl, n-but-3-enyl, n-but-1,3-dienyl, isobut-1-enyl(=2-methylprop-1-enyl), isobut-2-enyl, (=2-methylprop-2-enyl), sec-but-1-enyl(=1-methylprop-1-enyl). Preferred alkenyl radicals are ethenyl, n-prop-1-enyl, n-prop-2-enyl, n-but-1-enyl, n-but-2-enyl. One or more, for example 1, 2, 3, 4, 5, 6 or 7, hydrogen atoms in alkenyl radicals may be replaced by fluorine atoms. Substituted alkenyl radicals may be substituted in any positions.

Examples of cycloalkyl radicals are cyclopropyl, cyclobutyl, cyclopentyl. One or more, for example 1, 2, 3, 4, 5, 6, 7, 8 or 9 hydrogen atoms in cycloalkyl radicals may be replaced by fluorine atoms.

Methods for preparing the compounds of the formula I are also described. Thus, the compounds described by formula I can prepared in a manner known to the skilled worker from N-substituted cyanamides of the formula II and the appropriate ortho-phenylenediamines of the formula III, which are obtainable in large numbers by purchase or easily accessible by synthesis.

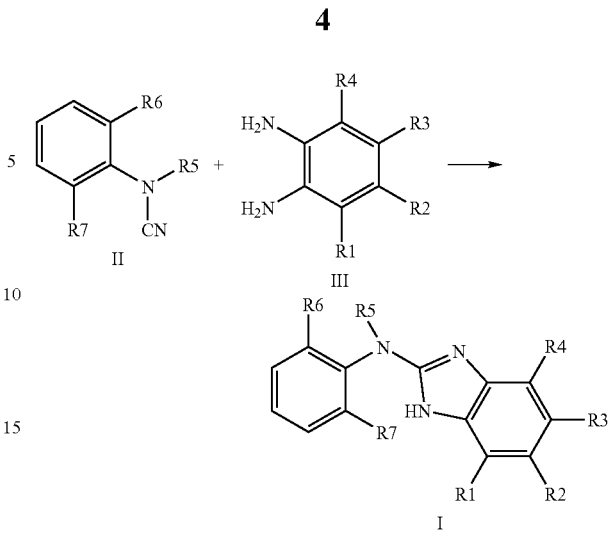

N-Substituted cyanamides of the formula II can be obtained by reacting the corresponding cyanamides IV with the compounds of R5-X. In this case, X is a group which can be replaced nucleophilically—such a chlorine, bromine, iodine, alkylsulfonate or arylsulfonate.

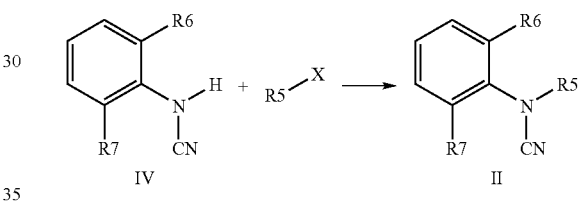

The required cyanamides IV can be prepared by various methods known from the literature (Chem. Ber. 1908, 41, 524, J. Med. Chem., 1975, 18, 90-99, Org. Lett. 2000, 795).

Alternatively, compounds of the formula I can also be prepared from N-substituted anilines of the formula V and benzoimidazole derivatives of the formula VI in a manner known from the literature.

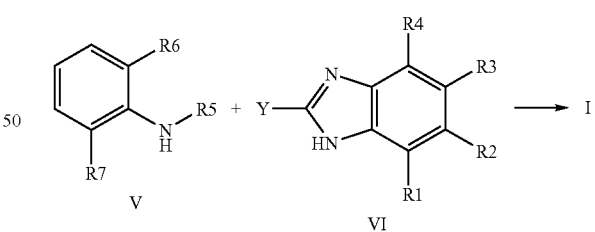

In this case, Y is a group that can be replaced nucleophilically, such as, for example, chlorine, bromine, iodine, alkylsulfonate such as, methanesulfonate or trifluoromethanesulfonate or arylsulphonate such as tosylate (analogous to Arch. Pharm. 1997, 330 (12) 372).

A further possibility is also to obtain the compounds of the formula I by reacting the 2-anilinobenzoimidazoles of the formula VII with compounds R5-X, where X is defined as described above. Compounds of the formula VII can be prepared by methods known from the literature (WO 02 46169, Synthesis 1983, 861).

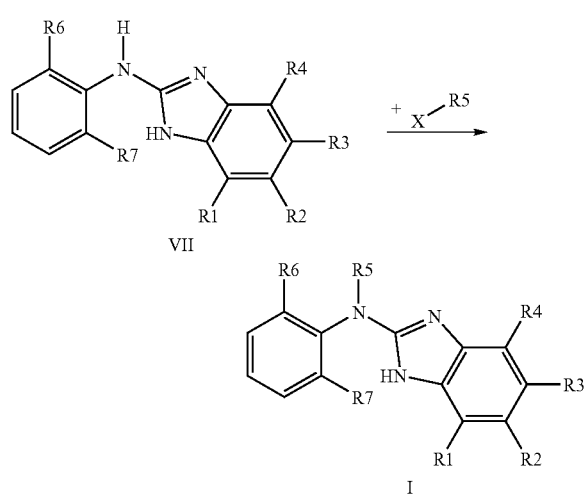

A further access to compounds of the formula I is provided by a synthetic sequence which starts from 2-nitrophenyl isothiocyanates of the formula VIII (J. Med. Chem. 1985, 28, 1925). The latter are reacted with amines of the formula V to give thioureas of the formula IX, which, after reduction, preferably with hydrogen in the presence of palladium/carbon or platinum dioxide or tin(IV) chloride and hydrochloric acid, provide the amino thioureas X, which are then cyclyzed to the compounds of the formula I, preferably in the presence of methyl iodide (MeI) or dicyclohexylcarbodiimide (DCCI), which may also be bound to a solid phase.

wise described as an NHE3 inhibitor (M. Donowitz et al., Am. J. Physiol. 276 (Cell Physiol. 45: C136-C144), does not act immediately like the compounds of formula I, but reaches its maximum strength of effect only after one hour.

German patent application DE10163239 proposes NHE3 inhibitors of the imidazolidine type. NHE3 inhibitors of the 2-phenylaminobenzoimidazole type have recently been disclosed (WO 02 46169).

Alkylations on the aniline nitrogen position in compounds of this type have, however, not previously been described.

German patent application DE 10224892 describes NHE3 inhibitors of the thiophene type. Japanese patent JP2869561 describes substituted benzoimidazoles for inhibiting platelet adhesion.

It has now been found, surprisingly, that alkylations of the aniline nitrogen do not lead to loss of the NHE3 activity. The hydrogen atom on the aniline nitrogen therefore appears not be essential for the NHE3 activity. Compared with the 2-phenylaminobenzoimidazoles described above, the compounds described herein are distinguished by greater lipophilicity, whereby the brain/plasma ratio is improved, which is particularly important for central indications.

Clonidine, which is similar to the compounds described herein, is known as a weak NHE inhibitor. Its effect on the rat NHE3 is indeed extremely moderate, with an $IC_{50}$ of 620 µM. Instead, it shows a certain selectivity for NHE2, for which it has an $IC_{50}$ of 42 µM (J. Orlowski et al J. Biol. Chem. 268, 25536). It should therefore rather be referred to as an NHE2 inhibitor. Besides the weak NHE effect, clonidine has a high affinity for the adrenergic alpha2 receptor and imidazoline I1 receptor, mediating a strong blood pressure-lowering effect (Ernsberger et al, Eur. J. Pharmacol. 134, 1, 1987).

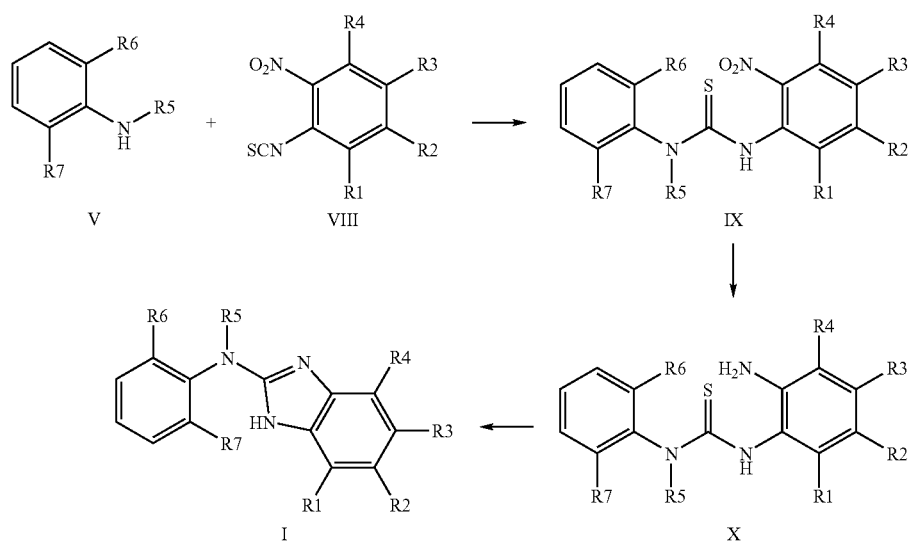

All substituents R1 to R7 mentioned in the synthetic processes have the meaning as defined for compounds of the formula I.

It was surprisingly possible to show in the present invention that the described compounds are potent inhibitors of the sodium/hydrogen exchanger (NHE), in particular of NHE3.

Known NHE3 inhibitors are derived, for example, from compounds of the acylguanidine type (EP 825 178), norbornylamine type (DE 199 60 204), 2-guanidinoquinazoline type (WO 01 79 186, WO 02 20496) or benzamidine type (WO 01 21582, WO 01 72 742). Squalamine, which is like- Compounds of the formula I are distinguished by an increased NHE3 activity.

NHE3 is found in the body of various species preferentially in the bile, the intestine and the kidney (Larry Fliegel et al, Biochem. Cell. Biol. 76: 735-741, 1998), but has also been detected in the brain (E. Ma et al. Neuroscience 79: 591-603).

On the basis of their unexpected NHE-inhibitory properties, the compounds of the formula I are suitable for the prevention and treatment of diseases caused by an activation or by an activated NHE. The use of the compounds of the invention relates to the prevention and treatment of acute and chronic diseases in veterinary and human medicine.

Thus, NHE inhibitors of the invention are suitable for the treatment of diseases caused by ischemia and/or by reperfusion.

The compounds described herein are, as a result of their pharmacological properties, outstandingly suitable as antiarrhythmic drugs with a cardioprotective component for prophylaxis of infarction and for treatment of infarction, and for the treatment of angina pectoris, in which connection they also inhibit or greatly reduce in a preventive manner the pathophysiological processes associated with the development of ischemia-induced damage, in particular in the induction of ischemia-induced cardiac arrhythmias. Because of their protective effects against pathological hypoxic and ischemic situations, the compounds of the formula I which are used according to the invention can, as a result of inhibition of the cellular $Na^+/H^+$ exchange mechanism, be used as drugs for the treatment of all acute or chronic damage induced by ischemia or disorders induced primarily or secondarily thereby. This relates to the use thereof as drugs for surgical interventions, e.g. in organ transplantations, in which cases the compounds can be used both to protect the organs in the donor before and during removal, to protect removed organs for example on treatment with or storage thereof in physiological bath fluids, as well as during the transfer into the recipient organism. The compounds are likewise valuable drugs with a protective action during the performance of angioplastic surgical interventions, for example on the heart as well as peripheral vessels.

In accordance with their protective action against ischemia-induced damage, the compounds are also suitable as drugs for the treatment of ischemias of the nervous system, especially of the CNS, in which connection they are suitable for example for the treatment of stroke or of cerebral edema.

In addition, the compounds of the formula I which are used according to the invention are likewise suitable for the treatment of types of shock, such as, for example, of allergic, cardiogenic, hypovolemic and bacterial shock.

In addition, the compounds induce an improvement in the respiratory drive and are therefore used to treat respiratory conditions associated with the following clinical conditions and diseases: disturbance of central respiratory drive (e.g. central sleep apneas, sudden infant death, postoperative hypoxia), muscle-related breathing disorders, breathing disorders after long-term ventilation, breathing disorders associated with altitude adaptation, obstructive and mixed type of sleep apneas, acute and chronic pulmonary disorders with hypoxia and hypercapnia.

The compounds additionally increase the tone of the muscles of the upper airways, so that snoring is suppressed.

A combination of an NHE inhibitor with a carbonic anhydrase inhibitor (e.g. acetazolamide), the latter inducing metabolic acidosis and thus itself increasing respiratory activity, proves to be advantageous due to an enhanced effect and reduced use of active ingredient.

The compounds described herein are additionally suitable as drugs for the therapy and prophylaxis of disorders and impairment induced by overexcitability of the central nervous system, especially for the treatment of epileptiform disorders, centrally induced clonic and tonic spasms, states of mental depression, anxiety disorders and psychoses. The NHE inhibitors described herein may moreover be used alone or in combination with other substances having antiepileptic activity or antipsychotic active ingredients, or carbonic anhydratase inhibitors, for example with acetazolamide, and with other inhibitors of NHE or of the sodium-dependent chloride-bicarbonate exchanger (NCBE).

It has emerged that the compounds used according to the invention have a mild laxative effect and accordingly can be used advantageously as laxatives or if there is a risk of constipation.

The compounds of the invention can additionally be used advantageously for the prevention and therapy of acute and chronic disorders of the intestinal tract caused by ischemic states in the intestinal region and/or by subsequent reperfusion. Such complications may be induced for example by inadequate bowel peristalsis, like those for example to be observed frequently after surgical interventions, associated with constipation or greatly reduced bowel activity.

It is additionally possible to prevent gallstone formation.

The compounds of the formula I used according to the invention are furthermore distinguished by a strong inhibitory effect on the proliferation of cells, for example of fibroblast cell proliferation and the proliferation of smooth vascular muscle cells. The compounds of the formula I are therefore suitable as valuable therapeutic agents for diseases in which cell proliferation represents a primary or secondary cause, and can therefore be used as antiatherosclerotic agents, agents to prevent late complications of diabetes, agents to prevent chronic renal failure, cancers, fibrotic disorders of the heart and also pulmonary fibrosis, hepatic fibrosis or renal fibrosis, organ hypertrophies and hyperplasias, for example of the heart and prostate and can thus be utilized for the prevention and treatment of (congestive) heart failure or for prostate hyperplasia or prostate hypertrophy.

The compounds of the invention are effective inhibitors of the cellular sodium-proton antiporter (Na/H exchanger) which is elevated in numerous disorders (essential hypertension, atherosclerosis, diabetes, etc.), also in those cells which are readily amenable to measurements, such as, for example, in erythrocytes, platelets or leukocytes. The compounds used according to the invention are therefore suitable as excellent and simple scientific tools, for example in their use as diagnostic aids for determining and distinguishing different types of hypertension, but also of atherosclerosis, of diabetes and late complications of diabetes, proliferative disorders etc.

The compounds of the formula I are moreover suitable for preventive therapy to prevent the development and for the treatment of high blood pressure, for example of essential hypertension, because they reduce or completely inhibit the reabsorption of NaCl in the tubular system of the kidneys. Accordingly, they are also outstandingly suitable as combination and formulation partners for drugs used for treating high blood pressure. Examples of possible combinations are diuretics having a thiazide-like action, loop diuretics, aldosterone and pseudoaldosterone antagonists, such as hydrochlorothiazide, indapamide, polythiazide, furosemide, piretanide, torasemide, bumetanide, amiloride, triamterene. The NHE inhibitors of the present invention can further be used in combination with ACE inhibitors such as, for example, ramipril, enalapril or captopril. Further beneficial combination partners are also β-blockers.

The described NHE inhibitors can likewise be used in the prevention and for the treatment of thrombotic disorders because, as NHE inhibitors, they are able to inhibit both platelet aggregation itself and, in addition, are able to inhibit or prevent the excessive release of coagulation mediators, in particular of von Willebrand factor. The NHE inhibitors of the present invention can therefore be combined with further anticoagulant active ingredients such as, for example, acetylsalicylic acid, thrombin antagonists, factor Xa antagonists, drugs with fibrinolytic activity, factor VIIa antagonists etc.

Combined use of the present NHE inhibitors with NCBE inhibitors is particularly beneficial.

It has additionally been found that NHE inhibitors show a beneficial effect on serum lipoproteins. It is generally acknowledged that blood lipid levels which are too high, so-called hyperlipoproteinemias, represent a considerable risk factor for the development of arteriosclerotic vascular lesions, especially coronary heart disease. The reduction of elevated serum lipoproteins therefore has exceptional importance for the prophylaxis and regression of atherosclerotic lesions. The compounds used according to the invention can therefore be used for the prophylaxis and regression of atherosclerotic lesions by eliminating a causal risk factor. The NHE inhibitors of the invention can also be combined in a beneficial manner with other antiarteriosclerotic active ingredients such as a substance from the class of fibrates, an upregulator of LD2 receptor activity such as MD-700 and LY295427 or a cholesterol or bile acid absorption inhibitor or an antihypercholesterolemic agent from the class of statins, such as, for example, pravastatin, lovastatin, simvastatin.

With this protection of the vessels against the syndrome of endothelial dysfunction, compounds of the formula I are valuable drugs for the prevention and treatment of coronary vasospasms, peripheral vascular diseases such as intermittent claudication, of atherogenesis and of atherosclerosis, of left-ventricular hypertrophy and of dilated cardiomyopathy, and thrombotic disorders.

Said compounds can likewise be used for the treatment of diseases caused by protozoa and are particularly suitable as antimalarials.

The compounds are additionally suitable for controlling sucking parasites such as mosquitoes, ticks, fleas and plant pests.

In accordance with their protective effects, the compounds are also suitable as drugs for maintaining health and prolonging life.

The NHE inhibitors described herein can generally be combined in a beneficial manner with other compounds regulating the intracellular pH, suitable combination partners being inhibitors of the carbonic anhydratase enzyme group, inhibitors of the bicarbonate ion-transporting systems such as the sodium-bicarbonate cotransporter or the sodium-dependent chloride-bicarbonate exchanger, and other NHE inhibitors, for example having an inhibitory effect on other NHE subtypes, because the pharmacologically relevant pH-regulating effects of the NHE inhibitors described herein can be enhanced thereby.

Said compounds are therefore advantageously used for producing a medicament for the prevention and treatment of sleep apneas and muscle-related respiratory disorders; for producing a medicament for the prevention and treatment of snoring; for producing a medicament for lowering blood pressure; for producing a medicament with a laxative effect for the prevention and treatment of intestinal blockages; for producing a medicament for the prevention and treatment of disorders induced by ischemia and reperfusion of central and peripheral organs, such as acute renal failure, stroke, endogenous states of shock, intestinal disorders etc.; for producing a medicament for the treatment of late damage from diabetes and chronic renal disorders, in particular of all inflammations of the kidneys (nephritides) which are associated with increased protein/albumin excretion; for producing a medicament for the treatment of hypercholesterolemia; for producing a medicament for the prevention of atherogenesis and of atherosclerosis; for producing a medicament for the prevention and treatment of diseases induced by elevated cholesterol levels; for producing a medicament for the prevention and treatment of diseases induced by endothelial dysfunction; for producing a medicament for the treatment of infestation by ectoparasites; for producing a medicament for the treatment of said disorders in combinations with hypotensive substances, preferably with angiotensin converting enzyme (ACE) inhibitors, with diuretics, aldosterone antagonists and angiotensin receptor antagonists. A combination of an NHE inhibitor of the formula I with an active ingredient lowering the blood lipid level, preferably with an HMG-CoA reductase inhibitor (e.g. lovastatin or pravastatin), the latter bringing about a hypolipidemic effect and thus increasing the hypolipidemic properties of the NHE inhibitor of the formula I, proves to be a beneficial combination with enhanced effect and reduced use of active ingredient.

The administration of sodium-proton exchange inhibitors of the formula I as novel drugs for lowering elevated blood lipid levels, and the combination of sodium-proton exchange inhibitors with hypotensive drugs and/or drugs with hypolipidemic activity is claimed.

The invention also relates to curative compositions for human, veterinary or phytoprotective use comprising an effective amount of a compound of the formula I and/or of a pharmaceutically acceptable salt thereof, as well as curative compositions for human, veterinary or phytoprotective use comprising an effective amount of a compound of the formula I and/or of a pharmaceutically acceptable salt thereof alone or in combination with one or more other pharmacological active ingredients or drugs.

Drugs which comprise a compound I can in this connection be administered orally, parenterally, intravenously, rectally, transdermally or by inhalation, the preferred administration being dependent on the particular characteristics of the disorder. The compounds of the formula I may moreover be used alone or together with pharmaceutical excipients, both in veterinary medicine and in human medicine, and in crop protection.

The excipients suitable for the desired pharmaceutical formulation are familiar to the skilled worker on the basis of his expert knowledge. Besides solvents, gel formers, suppository bases, tablet excipients, and other active ingredient carriers, it is possible to use, for example, antioxidants, dispersants, emulsifiers, antifoams, flavorings, preservatives, solubilizers or colors.

For a form for oral administration, the active compounds are mixed with additives suitable for this purpose, such as carriers, stabilizers or inert diluents, and converted by conventional methods into suitable dosage forms such as tablets, coated tablets, hard gelatin capsules, aqueous, alcoholic or oily solutions. Examples of inert carriers which can be used are gum arabic, magnesia, magnesium carbonate, potassium phosphate, lactose, glucose or starch, especially corn starch. It is moreover possible for the preparation to take place both as dry granules and as wet granules. Examples of suitable oily carriers or solvents are vegetable or animal oils such as sunflower oil or fish liver oil.

For subcutaneous or intravenous administration, the active compounds used are converted, if desired with the substances customary for this purpose, such as solubilizers, emulsifiers or other excipients, into a solution, suspension or emulsion. Examples of suitable solvents are: water, physiological saline or alcohols, e.g. ethanol, propanol, glycerol, as well as sugar solutions such as glucose or mannitol solutions, or else a mixture of the various solvents mentioned.

Suitable as pharmaceutical formulation for administration in the form of aerosols or sprays are, for example, solutions, suspensions or emulsions of the active ingredient of the formula I in a pharmaceutically acceptable solvent such as, in particular, ethanol or water, or a mixture of such solvents.

The formulation may, if required, also contain other pharmaceutical excipients such as surfactants, emulsifiers and stabilizers, and a propellant gas. Such a preparation normally contains the active ingredient in a concentration of about 0.1 to 10, in particular of about 0.3 to 3, % by weight.

The dosage of the active ingredient of the formula I to be administered, and the frequency of administration, depend on the potency and duration of action of the compounds used; additionally also on the nature and severity of the disorder to be treated and on the sex, age, weight and individual responsiveness of the mammal to be treated.

On average, the daily dose of a compound of the formula I for a patient weighing about 75 kg is at least 0.001 mg/kg, preferably 0.1 mg/kg, to a maximum of 50 mg/kg, preferably 1 mg/kg, of body weight. For acute episodes of the disorder, for example immediately after suffering a myocardial infarction, higher and, in particular, more frequent dosages may also be necessary, e.g. up to 4 single doses a day. Up to 200 mg/kg a day may be necessary, in particular on i.v. administration, for example for a patient with infarction in the intensive care unit.

Pharmaceutically acceptable salts are prepared for example via the following acids: from inorganic acids such as hydrochloric acid, sulfuric acid or phosphoric acid or from organic acids such as acetic acid, citric acid, tartaric acid, lactic acid, malonic acid, methanesulfonic acid, fumaric acid. Suitable acid addition salts are salts of all pharmacologically acceptable acids, for example halides, especially hydrochlorides, lactates, sulfates, citrates, tartrates, acetates, phosphates, methylsulfonates, p-toluenesulfonates, adipates, fumarates, gluconates, glutamates, glycerolphosphates, maleates and pamoates (this group also corresponds to the physiologically acceptable anions); but also to trifluoroacetates.

EXAMPLES

List of Abbreviations Used

| Rt | retention time |
|---|---|
| LCMS | liquid chromatography mass spectroscopy |
| MS | mass spectroscopy |
| ES+ | electrospray, positive mode |
| HPLC | high performance liquid chromatography |

General:

The retention times (Rt) stated below relate to LCMS measurements with the following parameters:

Analytical method:

stationary phase: Merck Purospher 3μ2×55 mm mobile phase: 95% $H_2O$ (0.1% HCOOH)→>95% acetonitrile (0.1% HCOOH); 5 min→95% acetonitrile (0.1% HCOOH); 2 min→95% $H_2O$ (0.1% HCOOH); 1 min; 0.45 ml/min.

The preparative HPLC was carried out under the following conditions:

stationary phase: Merck Purospher RP18 (10 μM) 250×25 mm mobile phase: 90% $H_2O$ (0.05% TFA)→90% acetonitrile; 40 min; 25 ml/min Example 1

(1H-Benzoimidazol-2-yl)(2,6-dichlorophenyl)ethylamine

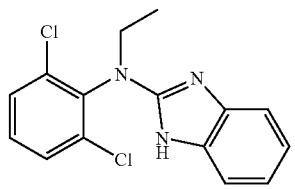

(1H-Benzoimidazol-2-yl)(2,6-dichlorophenyl)amine (350 mg) was dissolved in dimethylformamide (8 ml). Potassium carbonate (383 mg) was added to the resulting solution and, at 0° C., ethyl iodide (0.1 ml) was added dropwise while stirring. After stirring at 0° C. for half an hour, stirring was continued at room temperature. 2.5 hours later, the reaction mixture was added to ice-water, and the aqueous phase was extracted three times with ethyl acetate. The combined organic extracts were washed with saturated sodium chloride solution and subsequently dried over magnesium sulfate. The residue after the solvent had been stripped off in vacuo was purified by preparative HPLC. The product-containing fractions were combined, the acetonitrile was stripped off in a rotary evaporator, and the aqueous residue was neutralized with potassium carbonate and extracted three times with ethyl acetate. Drying over magnesium sulfate was followed by evaporation to dryness and chromatography on silica gel with dichloromethane/methanol 10/0.125. 12 mg of the desired compound were obtained.

LCMS-Rt: 2.25 min

MS (ES+, M+H+): 306.09

Example 2

(1H-Benzoimidazol-2-yl)(2,6-dichlorophenyl)methylamine hydrochloride

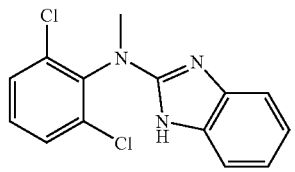

(1H-Benzoimidazol-2-yl)(2,6-dichlorophenyl)amine (500 mg) was dissolved in methanol (50 ml). Potassium carbonate (220 mg) was added to the resulting solution and, at room temperature, methyl iodide (248 mg) was added dropwise while stirring vigorously, and the mixture was then heated to reflux. After three days, the reaction mixture was concentrated, the residue was partitioned between ethyl acetate and water, and then the ethyl acetate phase was separated off and dried. The residue after concentration in vacuo was purified by preparative HPLC. The product-containing fractions were combined, the acetonitrile was stripped off in a rotary evaporator, and the aqueous residue was neutralized with potassium carbonate and extracted three times with ethyl acetate. Drying over magnesium sulfate was followed by evaporation to dryness and chromatography on silica gel with ethyl acetate/heptane 1/1. After the product-containing fractions had been combined and the solvent had been stripped off, the residue was taken up in aqueous hydrochloric acid and freeze dried. 85 mg of the desired compound were obtained.

LCMS-Rt: 2.03 min
MS (ES+, M+H+): 292.05

Alternatively, (1H-benzoimidazol-2-yl)(2,6-dichlorophenyl)methylamine hydrochloride can also be obtained as follows:

a) (2,6-Dichlorophenyl)methylcyanamide (2,6-Dichlorophenyl)cyanamide (1 g) was dissolved in dry dimethylformamide (25 ml), powdered potassium carbonate (739 mg) was added and then, while stirring, methyl iodide (1.52 g) was added dropwise. After stirring at room temperature for two hours, the reaction mixture was concentrated, the residue was taken up with water and extracted three times with ether, and the combined ether extracts were dried over magnesium sulfate. Filtration was followed by evaporation to dryness and purification of the residue by preparative HPLC. 600 mg of the desired product were isolated.

$^1$H-NMR (DMSO-d6/TMS, 400 MHz): 7.67 (d, 10 Hz, 2H), 7.50 (t, 10 Hz, 1H), 3.23 (s, 3H)

b) (1H-Benzoimidazol-2-yl)(2,6-dichlorophenyl)methylamine hydrochloride (2,6-Dichlorophenyl)methylcyanamide (150 mg) and phenylenediamine (81 mg) were dissolved in hexafluoro-2-propanol (1 ml) and heated at 100° C. in a closed vessel for 2 days. After a further day at 60° C. in an open vessel, the solvent was removed and the residue was purified by preparative HPLC. The product-containing fractions were combined, the acetonitrile was stripped off in a rotary evaporator, and the aqueous residue was neutralized with potassium carbonate and extracted three times with ethyl acetate. Drying over magnesium sulfate and purification with carbon were followed by evaporation to dryness. The residue was taken up in aqueous hydrochloric acid and freeze dried. 5 mg of the desired compound were obtained.

Example 3

(1H-Benzoimidazol-2-yl)(2,6-dichlorophenyl)isopropylamine

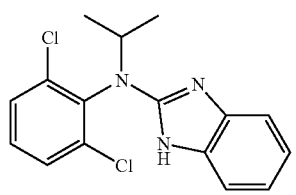

In analogy to example 1, (1H-benzoimidazol-2-yl)(2,6-dichlorophenyl)amine (250 mg) was dissolved in dimethylformamide (3 ml), deprotonated with sodium hydride (43 mg) and alkylated with isopropyl bromide (111 mg) in a closed vessel at 100° C. for one hour. Workup and chromatography resulted in 21 mg of the desired compound.

LCMS-Rt: 2.30 min
MS (ES+, M+H+): 320.16

Example 4

(2,6-Dichlorophenyl)(5-fluoro-1H-benzoimidazol-2-yl)methylamine

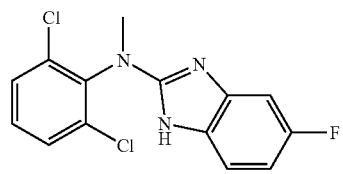

In analogy to example 1, (2,6-dichlorophenyl)(5-fluoro-1H-benzoimidazol-2-yl)amine (250 mg) was dissolved in dimethylformamide (2 ml), deprotonated with sodium hydride (45 mg) and alkylated with methyl iodide (120 mg) in a closed vessel at 100° C. Workup and chromatography resulted in 19 mg of the desired compound.

LCMS-Rt: 2.16 min
MS (ES+, M+H+): 310.12

Example 5

Allyl(1H-benzoimidazol-2-yl)(2,6-dichlorophenyl)amine

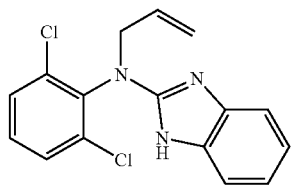

(1H-Benzoimidazol-2-yl)(2,6-dichlorophenyl)amine (250 mg) was dissolved in dimethylformamide (2 ml) under argon in a microwave-safe vessel, and sodium hydride (43 mg) was added. After stirring at room temperature for one hour, cyclopropyl bromide (109 mg) was added dropwise, and the mixture was stirred for a further half hour. The vessel was subsequently placed in the microwave apparatus firstly for 10 min (80° C., 100 W) and then for a further 60 min (110° C., 100 W). Further addition of cyclopropyl bromide (55 mg) was followed by placing in the microwave (110° C., 100 W) once again for 60 min.

Workup and silica gel chromatography (see example 1) resulted in 13 mg of the desired compound.

LCMS-Rt: 2.28 min
MS (ES+, M+H+): 318.20

Example 6

(1H-Benzoimidazol-2-yl)cyclopentyl(2,6-dichlorophenyl)amine

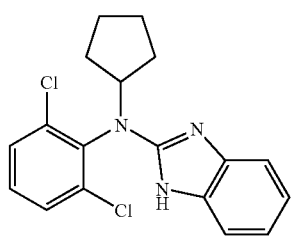

In analogy to example 1, (1H-benzoimidazol-2-yl)(2,6-dichlorophenyl)amine (250 mg) was dissolved in dimethylformamide (2 ml) at room temperature, deprotonated with sodium hydride (48 mg) and alkylated with cyclopentyl bromide (136.7 mg) in a closed vessel at 100° C. for 8 h. Workup and chromatography resulted in 38 mg of the desired compound.

LCMS-Rt: 2.60 min

MS (ES$^+$, M+H$^+$): 346.22

Experimentals

Description of Test

In this test, the recovery in the intracellular pH (pH$_i$) after an acidification was ascertained, which is initiated if the NHE3 is capable of functioning, even under bicarbonate-free conditions. For this purpose, the pH$_i$ was determined using the pH-sensitive fluorescent dye BCECF (Calbiochem, the precursor BCECF-AM is employed). The cells (fibroblasts, LAP1 cells) were initially loaded with BCECF. The BCECF fluorescence was determined in a "Ratio Fluorescence Spectrometer" (Photon Technology International, South Brunswick, N.J., USA) at excitation wavelengths of 505 and 440 nm and an emission wavelength of 535 nm and converted into the pH$_i$ using calibration curves. The cells were incubated in NH$_4$Cl buffer (pH 7.4) (NH$_4$Cl buffer: 115 mM NaCl, 20 mM NH$_4$Cl, 5 mM KCl, 1 mM CaCl$_2$, 1 mM MgSO$_4$, 20 mM Hepes, 5 mM glucose, 1 mg/ml BSA; a pH of 7.4 is adjusted with 1 M NaOH) even during the BCECF loading. The intracellular acidification was induced by adding 975 µl of an NH$_4$Cl-free buffer (see below) to 25 µl aliquots of the cells incubated in NH$_4$Cl buffer. The subsequent rate of pH recovery was recorded for three minutes. To calculate the inhibitory potency of the tested substances, the cells were initially investigated in buffers with which a complete or absolutely no pH recovery took place. For complete pH recovery (100%), the cells were incubated in Na$^+$-containing buffer (133.8 mM NaCl, 4.7 mM KCl, 1.25 mM CaCl$_2$, 1.25 mM MgCl$_2$, 0.97 mM Na$_2$HPO$_4$, 0.23 mM NaH$_2$PO$_4$, 5 mM Hepes, 5 mM glucose, a pH of 7.0 is adjusted with 1 M NaOH). To determine the 0% value, the cells were incubated in an Na$^+$-free buffer (133.8 mM choline chloride, 4.7 mM KCl, 1.25 mM CaCl$_2$, 1.25 mM MgCl$_2$, 0.97 mM K$_2$HPO$_4$, 0.23 mM KH$_2$PO$_4$, 5 mM Hepes, 5 mM glucose, a pH of 7.0 is adjusted with 1 M KOH). The substances to be tested were made up in the Na$^+$-containing buffer. The recovery of the intracellular pH at each test concentration of a substance was expressed as a percentage of the maximum recovery. The IC$_{50}$ value for the particular substance for the individual NHE subtypes was calculated from the pH recovery percentages using the Sigma-Plot program.

Results:

| Example | IC$_{50}$ [µM], (rNHE3) |
|---------|------------------------|
| 1       | 0.57                   |
| 2       | 0.53                   |
| 3       | 9.3                    |
| 4       | 3.3                    |
| 5       | 1.5                    |
| 6       | 8.3                    |

We claim:

1. A compound of formula I

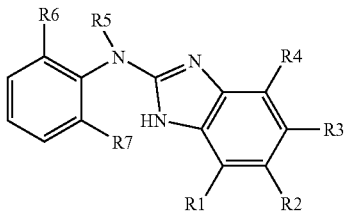

wherein,

R1 and R4 are independently H, F, Cl, Br, C$_1$-C$_4$-alkyl or C$_1$-C$_4$-alkoxy, wherein the C$_1$-C$_4$-alkyl and C$_1$-C$_4$-alkoxy are independently optionally substituted by 1, 2, 3, 4, 5, 6, 7, 8 or 9 fluorine atoms;

R2 and R3 are independently H, F, OH, C$_1$-C$_3$-alkyl or C$_1$-C$_3$-alkoxy, wherein the C$_1$-C$_3$-alkyl and C$_1$-C$_3$-alkoxy are independently optionally substituted by 1, 2, 3, 4, 5, 6 or 7 fluorine atoms;

R5 is C$_2$-C$_4$-alkenyl or C$_3$-C$_5$-cycloalkyl, wherein the C$_2$-C$_4$-alkenyl and C$_3$-C$_5$-cycloalkyl are independently optionally substituted by 1, 2, 3, 4, 5, 6, 7, 8 or 9 fluorine atoms; and R6 and R7 are independently F, Cl, Br, C$_1$-C$_4$-alkyl or C$_1$-C$_3$-alkoxy, wherein the C$_1$-C$_4$-alkyl and C$_1$-C$_3$-alkoxy are independently optionally substituted by 1, 2, 3, 4, 5, 6, 7, 8 or 9 fluorine atoms, or a pharmaceutically acceptable salt or trifluoroacetic acid salt thereof.

2. A compound which is:

allyl(1H-benzoimidazol-2-yl)(2,6-dichlorophenyl)amine; or (1H-benzoimidazol-2-yl)cyclopentyl(2,6-dichlorophenyl)amine;

or a pharmaceutically acceptable salt or trifluoroacetic acid salt thereof.

3. A pharmaceutical composition comprising the compound according to claim 1 or a pharmaceutically acceptable salt or trifluoroacetic acid salt thereof, and a pharmaceutically acceptable excipient or carrier.

4. A pharmaceutical composition comprising the compound according to claim 2 or a pharmaceutically acceptable salt or trifluoroacetic acid salt thereof, and a pharmaceutically acceptable excipient or carrier.

* * * * *